US007528234B2

(12) United States Patent
Fiume et al.

(10) Patent No.: US 7,528,234 B2
(45) Date of Patent: May 5, 2009

(54) PROCESS FOR THE PREPARATION OF DOXORUBICIN CONJUGATES WITH LACTOSAMINATED HUMAN ALBUMIN

(75) Inventors: Luigi Fiume, Bologna (IT); Giuseppina Di Stefano, Bologna (IT); Marcella Lanza, Bologna (IT)

(73) Assignee: Universita' Di Bologna, Bologna (IT)

( * ) Notice: Subject to any disclaimer, the term of this patent is extended or adjusted under 35 U.S.C. 154(b) by 0 days.

(21) Appl. No.: 11/579,857

(22) PCT Filed: May 4, 2005

(86) PCT No.: PCT/IT2005/000257

§ 371 (c)(1),
(2), (4) Date: Nov. 7, 2006

(87) PCT Pub. No.: WO2005/107814

PCT Pub. Date: Nov. 17, 2005

(65) Prior Publication Data

US 2007/0219351 A1    Sep. 20, 2007

(30) Foreign Application Priority Data

May 7, 2004    (IT)    .......................... MI04A000928

(51) Int. Cl.
*C07K 14/765* (2006.01)
*C07K 1/02* (2006.01)
*C07K 1/06* (2006.01)
(52) U.S. Cl. ...................................... 530/363; 530/402
(58) Field of Classification Search .................. 530/363, 530/402
See application file for complete search history.

(56) References Cited

FOREIGN PATENT DOCUMENTS

| WO | 93/25239 | 12/1993 |
| WO | 2006/074272 | 7/2006 |
| WO | 2007/039448 | 4/2007 |

OTHER PUBLICATIONS

Di Stefano, G., et al. 2003 Digestive and Liver Disease 35: 428-433.*
Kratz F., "Drug conjugates with albumin and transferrin", Expert Opinion on Therapeutic Patents, Ashley Publications, GB, vol. 12 No. 3, 2002, pp. 433-439.
Sewo Y-Y T et al., "Expression of a functional asialoglycoprotein receptor in human renal proximal tubular epithelial cells,"Nephron, XX, XX, vol. 91, No. 3, 2002, pp. 431-438.
Treré D., et al., "The asialoglycoprotein receptor in human hepatocellular carcinomas: Its expression on proliferating cells," British Journal of Cancer, London, GB, vol. 81, No. 3, 1999, pp. 404-408.
Saxena A. et al., "H2, the minor subunit of the human asialoglycoprotein receptor, traffics intracellular and forms homo-oligomers, but does not bind asialo-orosomucoid," Journal of Biological Chemistry, vol. 277, No. 38, 2002, pp. 35297-35304.

Fiume et al., "Doxorubicin coupled to lactosaminated albumin inhibits the growth of hepatocellular carcinomas induced in rats by diethylnitrosamine," Journal of Hepatology, Munksgaard International Publishers, Copenhagen, DK, vol. 43, No. 4, Oct. 2005, pp. 645-652.
Di Stefano, G. et al., "Enhanced uptake of lactosaminated human albumin by rat hepatocarcinomas: Implications for an improved chemotherapy of primary liver tumors," Liver International, Blackwell Munksgaard, Oxford, GB, vol. 25, No. 4, 2005, pp. 854-860.
Di Stefano et al., "Doxorubicin coupled to lactosaminated albumin: Enhanced drug levels in rat hepatocarcinomas," Digestive and Liver Disease, W.B. Saunders, vol. 38, No. 4, Apr. 2006, pp. 284-285.
Di Stefano G. et al., "A conjugate of doxorubicin with lactosaminated albumin enhances the drug concentrations in all the forms of rat hepatocellular carcinomas independently of their differentiation grade," Liver International, Blackwell Munksgaard, Oxford, GB, vol. 26, No. 6, 2006, pp. 726-733.
International Search Report, dated Jan. 19, 2006 for corresponding PCT Application No. PCT/IT2005/000257 (3 pages).
Written Opinion Search Report, dated Nov. 7, 2006 for corresponding PCT Application No. PCT/IT2005/000257 (3 pages).
International Search Report, dated Mar. 19, 2007 for corresponding PCT Application No. PCT/EP2006/066489 (6 pages).
Written Opinion, dated Mar. 20, 2008 for corresponding PCT Application No. PCT/EP2006./066489 (10 pages).
Di Stefano G et al: "Doxorubicin coupled to lactosaminated human albumin remains confined within house liver cells after the intracellular release from the carrier," Digestive and Liver Disease: Official Journal of the Italian Society of Gastroenterology and the Italian Association for the Study of the Liver, Jun. 2003, vol. 35, No. 6, pp. 428-433.

(Continued)

*Primary Examiner*—Maryam Monshipouri
*Assistant Examiner*—Marsha M Tsay
(74) *Attorney, Agent, or Firm*—Fredrikson & Byron, P.A.

(57) ABSTRACT

A procedure is described for conjugating the hydrazone derivatives of doxorubicin having a maleimide terminal group to lactosaminated human albumin (L-HSA). The procedure is based on the use of trialkyiphosphines to reduce the disulfide bonds of the protein and make its SH groups available for the formation of the thioether bond. In comparison with the conjugation obtained by using thiol reducing agents, such as dithiothreitol, this has the advantage that even when it is performed under very simple conditions, specifically without using an inert atmosphere, in the absence of oxygen, and without preliminary purification of the "reduced" L-HSA, it does not bring about the formation of a precipitate in the reaction means. In comparison with conjugation to L-HSA thiolated by using iminothiolane, the novel procedure has the advantage of greater simplicity and of not introducing exogenous molecules into the L-HSA in order to make the SH groups available.

11 Claims, 1 Drawing Sheet

OTHER PUBLICATIONS

Figure 1:
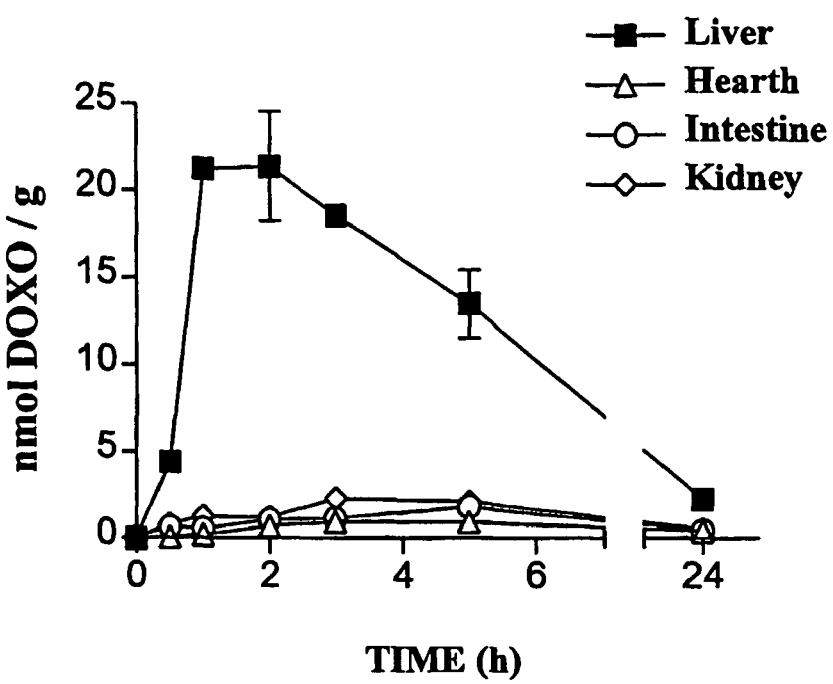

Meunier Laurent et al: "Optimized Conditions to couple two water-soluble biomolecules through alkylamine thiolation and thioetherification," Bioconjugate Chem., vol. 10, 1999, pp. 206-212.

Database Biosis Biosciences Information Service, Philadelphia, PA, us; Jan. 2004, Bhasin Nishant: "UNF chemistry on a single protein (VCAM-1) during forced unfolding by AFM," Database Accession No. PREV200400126455, Abstract.

Burmeister Getz E et al: "Comparison between the sulfhydryl reductants tris(20carboxyethyl) phosphine and dithiothreitol for use in proteinbiochemistry," Analytical Biochemistry, Academic Press, San Diego, CA, US, vol. 273, Aug. 15, 1999, pp. 73-80.

Shafer Douglas E et al: "Reaction of tris(2-carboxyethyl)phosphine (TCEP) with maleimide and alpha-haloacyl groups: Anomalous elution of TCEP by gel filtration," Analytical Biochemistry, vol. 282, No. 1, Jun. 15, 2000, pp. 161-164.

Kratz F et al: "Probin the cysteine034 position of endogenous serum albumin with thiol-binding doxorubicin derivatives. Improved efficacy of an acid-sensitive doxorubicin derivative with specific albumin-binding properties compared to that of the parent compound," Journal of Medicinal Chemistry, American Chemical Society, Washington, US, vol. 45, No. 25, Dec. 5, 2002, pp. 5523-5533.

Di Stefano G et al: "A novel method for coupling doxorubicin to lactosaminated human albumin by an acid sensitive hydrazone bond: synthesis, characterization and preliminary biological properties of the conjugate," European Journal of Pharmaceutical Sciences, Elsevier, Amsterdam, NL, vol. 23, No. 4-5, Dec. 2004, pp. 393-397.

Llovet J M., "Updated treatment approach to hepatocellular carcinoma", J Gastroenterol 2005; 40:225-235.

Mazue G, et al., "Anthracyclines: A review of general and special toxicity studies", Int J Oncol 1995; 7: 713-26.

Ashwell G, et al., "Carbohydrate-specific receptors of the liver", Ann Rev Biochem 1982; 51: 531-554.

Fiume L, et al., "Liver targeting of antiviral nucleoside analogs through the asialoglycoprotein receptor", J Viral Hep 1997; 4: 363-370.

Torrani Cerenzia M R, et al., "Adenine Arabinoside Monophosphate Coupled To Lactosaminated Human Albumin Administered for 4 Weeks in Patients With Chronic Type B Hepatitis Decreased Viremia Without Producing Significant Side Effects", Hepatology 1996; 23: 657-661.

Zarski J P, et al., "Efficacy and safety of lactosaminated human serum albumin-adenine arabinoside monophosphate in chronic hepatitis B patients non-responders to interferon therapy: a randomized clinical trial", J Hepatol 2001; 34: 487-488.

Greenfield R S, et al., "Evaluation in Vitro of Adriamycin Immunoconjugaates Synthesized Using an Acid-sensitive Hydrazone Linker", Cancer Res 1990; 50: 6600-6607.

Hyodo I, et al., "Distribution of asialoglycoprotein receptor in human hepatocellular carcinoma", Liver 1993; 13: 80-85.

Sawamura T, et al., "Hyperasialoglycoproteinemia in Patients With Chronic Liver Diseases and/or Liver Cell Carcinoma" Gastroenterology 1984; 87: 1217-1221.

Pittman R C, et al., "Radiolabeled Sucrose Covalently Linked to Protein" J Biol Chem. 1979; 254: 6876-6879.

Lowry O H et al., "Protein Measurement With the Folin Phenol Reagent" J Biol Chem 1951; 193: 265-275.

Wilson G., "Effect of Reductive Lactosamination On The Hepatic Uptake Of Bovine Pancreatic Ribonuclease A Dimer" J Biol Chem 1978; 253: 2070-2072.

Dubois M et al., "Colorimetric Method For Determination Of Sugars And Related Substances" Anal Chem 1956; 28: 350-356.

Willner D, et al., "(6-Maleimidocaproyl)hydrazone of Doxorubicin—A New Derivative for the Preparation of Immunoconjugates of Doxorubicin" Bioconj Chem 1993; 4: 521-527.

Schneider Y, et al., "Drug Targeting in Human Cancer Chemotherapy" Gregoriadis G et al., NATO ASI Series A: Life Sciences, Plenum Press New York 1984, 82: 1-25.

Fiume L, et al. Hepatocyte Targeting of Adenine-9-B-D-Arabinofuranoside 5'-Monophosphate (ara-AMP) Coupled to Lactosaminated Albumin, FEBS Lett 1981, 129:261-4.

Han JC and Han GY, A Procedure for Quantitative Determination of Tris(2-carboxyethyl)phosphine, an Odorless Reducing Agent More Stable and Effective Than Dithiothreitol, Anal Biochem 1994, 220: 5-10.

* cited by examiner

Distribution of free DOXO in mouse organs after intravenous injection of 1 µg/g of drug conjugated to L-HSA. Each item of data is the mean ± SE of the determinations in 3-4 animals.

PROCESS FOR THE PREPARATION OF DOXORUBICIN CONJUGATES WITH LACTOSAMINATED HUMAN ALBUMIN

CROSS REFERENCE TO RELATED APPLICATIONS

This application claims priority to prior International Application No. PCT/IT2005/000257, filed May 4, 2005, which claims priority to Italian Application No. MI2004A000928, filed May 7, 2004.

In order to reduce the extra-hepatic toxic effects of doxorubicin (DOXO) in the treatment of those hepatocarcinomas having cells which maintain the asialoglycoprotein receptor (ASGP-R) (Schneider Y, et al. "Drug targeting in human cancer chemotherapy", in Gregoriadis G et al., NATO ASI Series A: Life Sciences, Plenum Press New York 1984, 82: 1-25; Hoydo I, et al., "Distributor of asialoglycoprotein receptor . . . " Liver 1993, 13: 80-5; Trerè D, et al. "The asialoglycoprotein receptor . . . " Br J Cancer 1999, 81: 404-8.), the drug has been conjugated to lactosaminated human albumin (L-HSA) (Di Stefano G, et al. "Doxorubicin coupled to lactosaminated . . . " Dig Liver Dis 2003, 35: 428-33).

L-HSA is a neoglycoprotein which effects selective transport of drugs into hepatocytes, after having been bound and internalised by ASGP-R, which is present only on these cells (Fiume L, et al. "Hepatocyte targeting of adenine-9-β-D-arabinofuranoside . . . " FEBS Lett 1981, 129: 261-4; Torrani Cerenzia M R, et al. "Adenine arabinoside monophosphate . . . " Hepatology 1996, 23: 657-61; Zarski J P, et al. "Efficacy and safety of L-HSA-ara-AMP . . . " J Hepatol 2001, 34: 487-8).

Conjugation of DOXO to L-HSA has been achieved by using a derivative of DOXO characterised by a "linker" which is attached at one end to the drug with a hydrazone bond and, at the other end, bears a maleimide group which reacts with the SH groups of protein forming a thioether bond. The hydrazone bond is not broken at neutral pH, so ensuring the stability of the conjugate in the blood, but is rapidly hydrolysed at the acidic pH values of endosomes and lysosomes, so permitting rapid detachment of the drug once the conjugate has penetrated into the cells (Greenfield R S, et al. "Evaluation in vitro of adriamycin . . . " Cancer Res 1990, 50: 6600-7). The conjugation procedure described by Di Stefano G, et al. ("Doxorubicin coupled to lactosaminated . . . " Dig Liver Dis 2003, 35: 428-33) uses DOXO (6-maleimidocaproyl)hydrazone (DOXO-EMCH) as the DOXO derivative with "linkers" having the above-described features, DOXO-EMCH having already been described by Willner D, et al., "(6-Maleinimidocaproyl)hydrazone derivative of doxorubicin . . . " Bioconjug Chem 1993, 4: 521-7), which is incorporated herein by reference. Said procedure involves the preliminary introduction of SH groups into the L-HSA molecule by using iminothiolane (Meunier L, et al. "Optimized conditions to couple . . . " Bioconjug Chem 1999, 10: 206-12). This procedure has negative aspects, because the preparation of L-HSA thiolated by means of iminothiolane takes time and, above all, involves the introduction of exogenous molecules (iminothiolane, iodoacetamide) into the L-HSA.

DESCRIPTION OF THE INVENTION

The purpose of our research was to conjugate hydrazone derivatives of DOXO bearing the maleimide group (e.g.: DOXO-EMCH) without introducing new SH groups belonging to exogenous molecules into the L-HSA. In our first attempts, we attempted to make the SH groups of L-HSA available by reducing its disulfide bonds with the use of thiol reducing agents, such as dithiothreitol (DTT) and mercaptoethanol, as described in patent application EP-665020 (Bristol Myers Squibb), in which DOXO-EMCH is conjugated to immunoglobulins directed against surface antigens of neoplastic cells. EP-665020 describes two procedures. In the first, after reduction of the protein's disulfide groups ("reduced protein"), the reducing agent is removed before the protein is reacted with the DOXO-EMCH. In the second, after reduction of the protein's disulfide groups, the protein is reacted directly with the DOXO-EMCH. Both of the processes are carried out in an inert environment, in the absence of oxygen. United States patent U.S. Pat. No. 5,622,929, in contrast, reports a similar conjugation procedure which is performed in a normal atmosphere, without removal of oxygen. Due to its much greater simplicity, we followed the conjugation procedure which involves neither prior purification of the reduced protein nor an inert environment without oxygen. However, under all the tested reaction conditions (see below) using mercaptoethanol as reducing agent, virtually no DOXO-EMCH was conjugated to the L-HSA. On the other hand, when DTT was used as the reducing agent, we always obtained the unwanted effect of the formation of a large precipitate arising from the reaction of the DTT with the DOXO-EMCH which we could not manage to remove without losing a large percentage of the conjugate. Furthermore, the conjugates obtained when using DTT were highly polymerised.

We observed that these disadvantages could be overcome by replacing the thiol reducing agents with non-thiol reducing agents, such as trialkylphosphines.

The object of the invention is accordingly represented by a procedure for conjugating DOXO-EMCH, the structural formula of which is shown below,

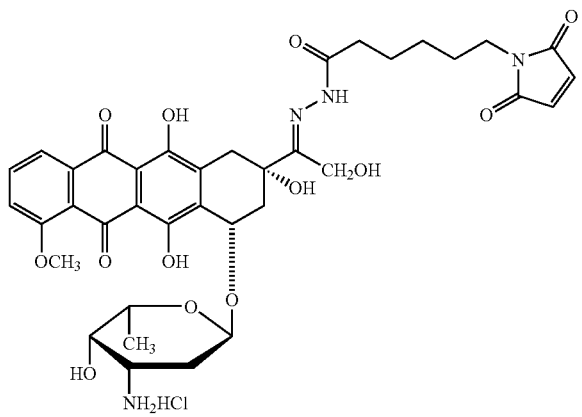

with L-HSA in the presence of a trialkylphosphine; a further object of the invention is represented by the conjugates obtained in said manner.

Among the trialkylphosphines, the best results (highest drug/L-HSA molar ratio, with reduced polymerisation of the protein) were obtained with tris(2-carboxyethyl)phosphine (TCEP).

The conjugation reaction is carried out in aqueous solution. It is carried out in a solution buffered to a pH of between 7 and 9.5, more preferably of between 8.5 and 9.5 and, still more preferably, of between 8.9 and 9.1. The reaction temperature is normally between +10° and +40° C., and preferably between +25° and +37° C., for a period of between 20 and 60 minutes.

According to a preferred aspect, the reaction is carried out using a concentration of between 2.5 and 4 mM of DOXO-EMCH, preferably of approx. 3.2 mM, a concentration of between 0.1 and 0.15 mM of L-HSA, preferably of approx. 0.125 mM, and a concentration of between 1.5 and 3.5 mM of TCEP.

Materials and Methods

Conjugation Reaction

The chemicals were obtained from Sigma-Aldrich (St. Louis, Mo., USA).

The human albumin (HSA) obtained from Kedrion (Lucca, Italy) was gel-filtered and the monomer was collected and used. The α-lactose was conjugated to the ε-$NH_2$ groups of the lysine residues of the HSA by means of reductive amination (Wilson G. "Effect of reductive lactosamination . . . " J Biol Chem 1978, 253: 2070-2.). The lactose/HSA molar ratio, measured as described by Wilson (Wilson G. "Effect of reductive lactosamination . . . " J Biol Chem 1978, 253: 2070-2), varied from 24 to 28 in the various preparations. The DOXO-EMCH was synthesised according to Willner et al. (Willner D, et al. "(6-maleinimidocaproyl)hydrazone derivative . . . " Bioconjug Chem 1993; 4: 521-7). DTT and mercaptoethanol were used as thiol reducing agents; among the trialkylphosphines, the most used was tris(2-carboxyethyl) phosphine (TCEP) which provided the best results and which has the advantage of being soluble in water and of not releasing toxic and foul-smelling vapours (Han J C and Han G Y. "A procedure for quantitative determination . . . " Anal Biochem 1994; 220: 5-10). The conjugation reactions were performed under different conditions with regard to pH (7, 8 and 9), temperature (17°, 27° and 37° C.) and with different concentrations of reducing agent (1.5 mM or 3.5 mM). In some preparations, the DOXO-EMCH (3.2 mM) was added in repeated aliquots, while in others the entire quantity was added at the beginning of the reaction.

The conditions which yielded the best results are stated below.

The conjugation reaction was performed at 27° C. with moderate stirring of the medium and lasted 30 min. 100 mg of L-HSA (1.25 μmol) are dissolved in 9.5 ml of 0.1 M sodium carbonate buffer, pH 9. 10 mg of TCEP (35 μmol) in 0.5 ml of sodium carbonate buffer are added to the L-HSA solution. The DOXO-EMCH (28 mg/ml in dimethylformamide) is added in aliquots of 75 μl every 2.5 min (total quantity added: 25 mg, 32 μmol). 2.5 minutes after the final addition, the conjugate is purified by gel-filtration through a Sephadex G25 (1.6×100 cm) column (Amersham), equilibrated and eluted with 0.2 M $NH_4HCO_3$. The molar ratio of the conjugate (moles of DOXO per mole of L-HSA) (MR) was calculated by measuring the L-HSA by the method of Lowry et al. (Lowry O H et al. "Protein measurement . . . ", J Biol Chem 1951; 193: 265-75) and the DOXO by means of absorbance at $\lambda_{495}$ [$\epsilon_{495}$ (pH 7.4) of DOXO-EMCH=9250 $M^{-1}$ $cm^{-1}$].

SDS-PAGE of Conjugates

Electrophoresis of the HSA, L-HSA and DOXO conjugates was performed by the method of Weber and Osborn (Weber K, et al. "The reliability of molecular weight determinations . . . " J Biol Chem 1969, 244: 4406-12), using a gel containing 5% acrylamide, 0.07% methylene bisacrylamide and 0.3% sodium dodecyl sulfate. After staining with Coomassie Blue R250, the gels were photographed and the bands were subjected to densitometric analysis using Kodak Digital Science 1D software.

Biological Studies

Female Swiss mice weighing 26-30 g were used. They were obtained from Harlan Italy (Udine) and were kept in the animal house at the Department of Experimental Pathology of the University of Bologna. The experimental protocols were approved by the University of Bologna's ethics committee.

The stability of the bond between DOXO and L-HSA in mouse plasma in vitro and the distribution of free DOXO (released from the "carrier") in the organs of the mice injected with the conjugate were studied as described in Di Stefano et al. (Di Stefano G, et al. "Doxorubicin coupled to lactosaminated human albumin . . . " Dig Liver Dis 2003, 35: 428-33).

RESULTS

Chemical Characteristics of the Conjugate

The procedure described in detail in "Materials and Methods" yielded reproducible results. In twenty preparations of L-HSA-DOXO, the drug/"carrier" molar ratio (MR) varied from 5 to 6.5. After freeze-drying, these preparations were readily dissolved in 0.9% NaCl at a concentration of 2 mg of DOXO conjugate/ml (corresponding to 40-55 mg of conjugate/ml), yielding clear solutions.

SDS-PAGE revealed that more than 70% of the L-HSA-DOXO conjugates consisted of the monomer of L-HSA and that the polymers were represented only by L-HSA dimer and trimer. L-HSA-DOXO incubated at pH 2 for 30 min released all the conjugated drug, which, when investigated by HPLC, exhibited only one peak which is co-eluted with an authentic sample of DOXO.

Conjugates prepared under the conditions described above, but at pH 8 or at a temperature of 37° C. had a higher MR (7-9), but exhibited a considerable degree of polymerisation. After freeze-drying, they did not dissolve completely in 0.9% NaCl.

When DTT was used, a substantial precipitate formed due to the reaction of the DOXO-EMCH with the SH groups of this reducing agent. The precipitate was removed by centrifugation and subsequent absorption on carbon prior to chromatographic purification of the conjugate. This removal procedure involved the loss of a high percentage of conjugate. Under all the conditions used for the conjugation reaction (see "Materials and Methods"), the conjugates prepared with DTT proved to be highly polymerised, with a fraction of the preparation which did not even enter into the polyacrylamide gel. When mercaptoethanol was used as the reducing agent, virtually no DOXO-EMCH conjugated to the L-HSA (MR<1).

Biological Studies

In accordance with the data of Greenfield et al., (Greenfield R S, et al. "Evaluation in vitro of adriamycin . . . " Cancer Res 1990, 50: 6600-7) on the stability of the hydrazone bond at neutral pH, L-HSA-DOXO, when incubated for 2 h at 37° C. in mouse plasma, did not release a measurable quantity of drug. FIG. 1 shows the concentrations of free DOXO (released from the "carrier") in mouse organs at different times after intravenous administration of 24 μg/g of conjugate. This dose of conjugate corresponded a 1 μg/g of DOXO, which is a therapeutically effective dose.

The concentrations of DOXO in the liver proved to be quite a number of times higher than those measured in the other organs. These results are comparable with those obtained with the conjugate prepared using the previous procedure which made use of L-HSA thiolated by using iminothiolane (Di Stefano G, et al. "Doxorubicin coupled to lactosaminated human albumin . . . " Dig Liver Dis 2003, 35: 428-33). The high level of drug achieved in the liver only 60 min after administration of L-HSA-DOXO confirms the speed at which the hydrazone bond is broken down within the cell, which amounts to a definite advantage over the peptide bond used by some authors to bind DOXO to macromolecular "carriers" (O'Hare K B, et al. "Effect of galactose on interaction of N-(2-hydroxypropyl)methacrylamide . . . " Hepatology 1989, 10: 207-14). It has indeed recently been observed that conjugates prepared with the peptide "linker" do not release the drug once they have penetrated into the cells (Hovorka O, et al. "Difference in the intracellular fate . . . " J Control Release 2002, 80: 101-17).

CONCLUSIONS

The procedure for conjugating DOXO-EMCH to L-HSA using di/trialkylphosphines is very simple, quick and yields reproducible results. In comparison with the conjugation obtained by using DTT as reducing agent, this procedure has the advantage that even when it is performed under very simple conditions, specifically without using an inert atmosphere, in the absence of oxygen, and without preliminary purification of the "reduced" L-HSA, it does not bring about the formation of a precipitate in the reaction means and produces conjugates with a low degree of polymerisation. Under the same conditions of use, DTT causes a precipitate which must be removed before chromatographic purification of the conjugate with loss of a high percentage of the conjugate itself and produces conjugates which are considerably polymerised. In comparison with the conjugate synthesised using L-HSA thiolated by using iminothiolane (Di Stefano G. et al., "Doxorubicin coupled to lactosaminated human albumin . . . ", Dig Liver Dis 2003; 35: 428-33), the conjugate obtained with the procedure described here has the advantage of not containing exogenous molecules in the L-HSA which have been introduced to make the SH groups available. The conjugate obtained with the procedure described here is a novel molecule consisting solely of L-HSA and the hydrazone derivative of DOXO attached to the protein with a thioether bond.

The invention claimed is:

1. A process for preparing doxorubicin conjugates with lactosaminated human albumin comprising conjugating doxorubicin (6-maleimidocaproyl)hydrazone with lactosaminated albumin in the presence of at least one trialkylphosphine which reduces the disulfide bonds of lactosaminated human albumin, said process being characterized in that no SH groups belonging to exogenous molecules are introduced into the lactosaminated human albumin.

2. A process according to claim 1, characterised in that said at least one trialkyiphosphine is tris(2-carboxyethyl)phosphine.

3. A process according to claim 1, characterised in that it is performed in aqueous solution.

4. A process according to claim 3, characterised in that it is carried out in a solution buffered to a pH of between 7 and 9.5.

5. A process according to claim 4, characterised in that it is performed at a pH of between 8.5 and 9.5.

6. A process according to claim 1, characterised in that it is carried out at a temperature of between +10° and +40° C.

7. A process according to claim 1, characterised in that it is performed for a period of between 20 and 60 minutes.

8. A process according to claim 1, characterised in that the doxorubicin (6-maleimidocaproyl) hydrazone has a concentration of between 2.5 and 4 mM, the lactosaminated human albumin has a concentration of between 0.1 and 0.15 mM and said at least one trialkylphosphine has a concentration of between 1.5 and 3.5 mM.

9. A process according to claim 8, characterised in that the doxorubicin (6-maleimidocaproyl)hydrazone has a concentration of approximately 3.2 mM and the lactosaminated human albumin has a concentration of approximately 0.125 mM.

10. Conjugates obtainable by the process according to claim 1.

11. A process according to claim 1, characterised in that it is carried out without using an inert atmosphere.

* * * * *